(12) United States Patent
Hassan et al.

(10) Patent No.: US 7,582,679 B2
(45) Date of Patent: Sep. 1, 2009

(54) COMPOSITIONS CONTAINING SOLID IBUPROFEN CONCENTRATES AND METHODS OF MAKING SOLID IBUPROFEN CONCENTRATES

(75) Inventors: Emadeldin Hassan, Cockeysville, MD (US); Sridhar Gumudavelli, Cockeysville, MD (US); David Goldman, Glen Arm, MD (US)

(73) Assignee: Pharmaceutics International Incorporated, Hunt Valley, MD (US)

( * ) Notice: Subject to any disclaimer, the term of this patent is extended or adjusted under 35 U.S.C. 154(b) by 364 days.

(21) Appl. No.: 11/346,975

(22) Filed: Feb. 3, 2006

(65) Prior Publication Data

US 2007/0184100 A1  Aug. 9, 2007

(51) Int. Cl.
*A61K 31/19* (2006.01)
(52) U.S. Cl. ..................................... 514/570
(58) Field of Classification Search .................. 514/570
See application file for complete search history.

(56) References Cited

U.S. PATENT DOCUMENTS

| | | | |
|---|---|---|---|
| 3,385,886 A | | 5/1968 | Stuart et al. |
| 4,609,675 A | * | 9/1986 | Franz .......................... 514/568 |
| 4,690,823 A | | 9/1987 | Lohner et al. |
| 4,861,797 A | | 8/1989 | Hass |
| 4,981,995 A | | 1/1991 | Elango et al. |
| 5,071,643 A | | 12/1991 | Yu et al. |
| 5,080,907 A | | 1/1992 | Iijima et al. |
| 5,376,688 A | | 12/1994 | Morton et al. |
| 5,468,502 A | | 11/1995 | Argiriadi et al. |
| 5,631,296 A | | 5/1997 | Birrenbach et al. |
| 6,596,312 B1 | | 7/2003 | Erkoboni et al. |
| 2003/0232097 A1 | * | 12/2003 | Radhakrishnan et al. .... 424/731 |

FOREIGN PATENT DOCUMENTS

WO  WO 93/11753 A1  6/1993
WO  WO 2006/100281 A  9/2006

OTHER PUBLICATIONS

European Patent Office, International Search Report and Written Opinion of the International Searching Authority in International Application No. PCT/US2007/061559 (Feb. 2, 2007).
Hannula, et al., "Effects of pH regulators used as additives on the bioavailability of ibuprofen from hard gelatin capsules," *European Journal of Drug Metabolism and Pharmacokinetics*, 3: 221-227 (1991).
Neuvonen et al., "Enhancement of Drug Adsorption by Antacids: An Unrecognised Drug Interaction," *Clinical Pharmacokinetics*, 27(2): 120-128 (1994).
Shaw et al., "The Effect of Selected Water-Soluble Excipients on the Dissolution of Paracetamol and Ibuprofen," *Drug Development and Industrial Pharmacy*, 31 (6): 515-525 (Jul. 2005).
International Preliminary Report on Patentability in International Application No. PCT/US2007/061559, dated Aug. 5, 2008.
S. K. Dwivedi et al., Int. J. Pharm. 87:95-104 (1992).

* cited by examiner

*Primary Examiner*—Raymond J Henley, III
(74) *Attorney, Agent, or Firm*—Leydig, Voit & Mayer, Ltd.

(57) ABSTRACT

The present invention is directed to a solid ibuprofen concentrate composition and method of producing the composition. The solid ibuprofen concentrate contains (a) a solid ibuprofen free acid and (b) a solid ibuprofen alkali salt, and is characterized in that at least 90% of the weight of the solid ibuprofen concentrate is ibuprofen free acid and ibuprofen alkali salt.

38 Claims, No Drawings

US 7,582,679 B2

COMPOSITIONS CONTAINING SOLID IBUPROFEN CONCENTRATES AND METHODS OF MAKING SOLID IBUPROFEN CONCENTRATES

BACKGROUND OF THE INVENTION

The medical need to design immediate release analgesics has been a continuous goal and challenge to the pharmaceutical industry. For example, ibuprofen, a powerful anti-inflammatory, analgesic, and antipyretic agent, has been formulated into different immediate release dosage forms such as tablets, capsules, effervescent granules, and solutions. However, the poor aqueous solubility and the very bitter taste of ibuprofen have limited formulation options.

Available techniques to manufacture immediate release oral ibuprofen pharmaceuticals can be classified into two major categories. The first category of techniques includes various solvent systems to prepare ibuprofen solutions that can be used as bulk liquids or can be filled into hard or soft capsules. A typical example of the solvent systems technique is described in U.S. Pat. No. 4,690,823 (Lohner et al.), where ibuprofen solutions are prepared with the aid of a polyoxyethylene-polyoxypropylene polymer or in a mixture of a polyalkylene glycol and a surfactant, such as polyoxyethylene-(40)-glycerol trihydroxystearate polyoxyethylene-(20)-stearyl alcohol or polyoxyethylene-(20)-sorbitan monostearate.

Other examples of the solvent systems technique are described in U.S. Pat. No. 5,071,643 (Yu et al.) and U.S. Pat. No. 5,376,688 (Morton et al.). The solvent systems consist of polyethylene glycol or other polymers such as diethylene glycol monoethyl ether, polyglycerol oleate, and mixtures thereof, containing 0.2 to 1.0 mole equivalents of a strong base consisting of the hydroxide form per mole of ibuprofen. The solvent systems additionally use ionizing agents, such as potassium hydroxide, sodium hydroxide, and ammonium hydroxide.

Other solvent systems are described in U.S. Pat. No. 5,468,502 (Argiriadi et al.), where surfactants and ammonium acetate are used to dissolve ibuprofen.

While the above examples of oral ibuprofen products can contain up to 67% w/w ibuprofen, they are mainly for capsule filling, and cannot be used directly for bulk oral solutions because of their unpleasant taste. In addition, the use of ionizing agents usually requires long period of time, vigorous mixing, and/or application of heat, due to the slow ionization in the non-aqueous media used.

U.S. Pat. No. 4,861,797 (Hass) has described a solvent system for ibuprofen where a clear and palatable liquid solution is made in an aqueous medium containing bicarbonate and methylcellulose. However, the ibuprofen solutions only contain a maximum ibuprofen concentration of only 8%.

The second category of techniques for manufacturing immediate release oral ibuprofen products is based on solid powders or granules that can be filled in two piece capsules or compressed into tablets. For this technique, binders are always required to increase powder density and enlarge particle size. Since binders usually act against immediate drug release, low molecular weight water soluble polymeric binders are often used. U.S. Pat. No. 6,596,312 (Erkoboni et al.) describes the use of hydrolyzed polysaccharide (i.e., cellulose hydrolyzate) as a binder for immediate release tablets. Similarly, U.S. Pat. No. 5,080,907 (Iijima et al.) describes the use of hydrolyzed proteins such as gelatin hydrolyzate for tablets and dry powder for suspension. Such powders or granules use relatively high amounts of the polymeric binders, which results in low drug concentrations.

In view of the foregoing limitations, there remains a need for oral ibuprofen products with higher drug concentrations, as well as methods of manufacturing the oral ibuprofen products. The invention provides such oral ibuprofen products, as well as production methods thereof.

BRIEF SUMMARY OF THE INVENTION

The invention provides a composition comprising a solid ibuprofen concentrate, wherein the solid ibuprofen concentrate comprises (a) a solid ibuprofen free acid and (b) a solid ibuprofen alkali salt, and wherein at least 90% of the weight of the solid ibuprofen concentrate is ibuprofen free acid and ibuprofen alkali salt.

The invention also provides a method of manufacturing a solid ibuprofen concentrate, wherein at least 90% of the weight of the solid ibuprofen concentrate is ibuprofen free acid and ibuprofen alkali salt, comprising: (a) mixing an ibuprofen free acid with a first alkaline substance to form a first composition; (b) mixing the first composition with a second alkaline substance to form a second composition; and (c) drying the second composition to produce the solid ibuprofen concentrate.

The invention further provides a method of formulating a solid ibuprofen concentrate into a soft gelatin capsule, wherein the solid ibuprofen concentrate comprises (a) a solid ibuprofen free acid and (b) a solid ibuprofen alkali salt, and wherein at least 90% of the weight of the solid ibuprofen concentrate is ibuprofen free acid and ibuprofen alkali salt, comprising: (a) dissolving the ibuprofen concentrate in a soft capsule vehicle to form a soft gelatin fill; and (b) encapsulating the soft gelatin fill in a soft gelatin capsule.

Additionally, the invention provides a composition comprising a solid ibuprofen concentrate, wherein the solid ibuprofen concentrate comprises (a) a solid ibuprofen free acid and (b) a solid ibuprofen alkali salt, and wherein at least 90% of the weight of the solid ibuprofen concentrate is ibuprofen free acid and ibuprofen alkali salt, wherein the ibuprofen alkali salt is produced from a solid ibuprofen free acid using at least two alkaline substances.

DETAILED DESCRIPTION OF THE INVENTION

The invention provides a highly concentrated ibuprofen composition in the solid state (herein referred to as a solid ibuprofen concentrate), as well as a process of manufacturing the composition. The composition comprises a solid ibuprofen concentrate, wherein the solid ibuprofen concentrate comprises (a) a solid ibuprofen free acid and (b) a solid ibuprofen alkali salt, and wherein at least 90% (e.g., at least about 92%, at least about 95%, at least about 97%, at least about 98%, or at least about 99%) of the weight of the solid ibuprofen concentrate is ibuprofen free acid and ibuprofen alkali salt.

The solid ibuprofen concentrate comprises (a) a solid ibuprofen free acid, and (b) a solid ibuprofen alkali salt. The ibuprofen free acid and ibuprofen alkali salt may be present in any suitable amount. Preferably, the solid ibuprofen comprises about 30-60% ibuprofen free acid and about 40-70% ibuprofen alkali salt. The solid ibuprofen alkali salt can be generated by any suitable process, such as from ibuprofen free acid during the process of granulation or as a result of an in-situ reaction of ibuprofen free acid with a hydroxide and carbonate. Preferably, 40-70% of the ibuprofen free acid is converted to ibuprofen alkali salt, and more preferably 50-60% is converted (e.g., 55%).

The ibuprofen free acid present in the solid ibuprofen concentrate can be prepared by conventional methods, for example, as described in U.S. Pat. Nos. 3,385,886 and 4,981,995. Alternatively, the ibuprofen free acid can be from any suitable source, such as BASF Aktiengesellschaft of Ludwigshafen, Germany.

The solid ibuprofen alkali salt can be any suitable ibuprofen alkali salt, such as ibuprofen potassium salt, ibuprofen sodium salt, ibuprofen ammonium salt, or a mixture thereof. Preferably, the solid ibuprofen alkali salt is an ibuprofen potassium salt. The solid ibuprofen alkali salt can be prepared by any suitable method, including the methods described herein.

The solid ibuprofen concentrate can be formulated into any suitable oral dosage form, such liquid and solid dosage forms. Preferably, the solid ibuprofen concentrate is formulated into ibuprofen-containing suspensions, solutions, drops, syrups, two-piece hard shell capsules, soft gelatin capsules, and tablets.

The invention further provides a method of manufacturing the solid ibuprofen concentrate of the invention. The starting material is solid ibuprofen free acid which is also referred to herein as ibuprofen powder. The method comprises the mixing an ibuprofen powder (i.e., a solid ibuprofen free acid) with at least two alkaline substances.

The method of the invention comprises mixing a solid ibuprofen free acid with a first alkaline substance. The first alkaline substance preferably is a highly water soluble material or mixture of materials that can be mixed in dry state with ibuprofen powder to form a dry powder mixture. The mixing can be achieved using any suitable mixing apparatus, such as by use of common powder blenders known in the art. For example, suitable mixing apparatus include gravity-dependent mixers, such as double cone mixers or V-blenders, and mechanical enforcement mixers, such as high speed-high shear mixers (e.g., a T. K. Fielder) or low speed planetary blenders. Preferably, the first alkaline substance interacts with solid ibuprofen powder in the presence of an aqueous fluid (e.g., water) at the solid-solid inter-phase between ibuprofen and the first alkaline substance.

The first alkaline substance can be any suitable alkaline substance, and is preferably a highly soluble material or mixture of materials. Suitable first alkaline substances include carbonate species, bicarbonate species, and mixtures thereof. Preferably, the first alkaline substance is selected from the group consisting of ammonium carbonate, ammonium bicarbonate, potassium carbonate, potassium bicarbonate, sodium carbonate, sodium bicarbonate, and mixtures thereof. More preferably, the first alkaline substance is potassium carbonate.

The amount of the first alkaline substance used in the method can be any suitable amount. Preferably, the amount of the first alkaline substance is about 0.1 to about 0.9 (e.g., about 0.2, about 0.3, about 0.4, about 0.5, about 0.6, about 0.7, about 0.8) mole equivalent to the amount of ibuprofen, and most preferably about 0.3 to about 0.6 mole equivalent to the amount of ibuprofen.

The mixture of the ibuprofen powder and the first alkaline substance is then mixed with a second alkaline substance. The second alkaline substance can be any suitable alkaline substance, such as a hydroxide species. Preferably, the second alkaline species is selected from the group consisting of ammonium hydroxide, potassium hydroxide, sodium hydroxide, and mixtures thereof. More preferably, the second alkaline substance is potassium hydroxide.

The amount of the second alkaline substance can be any suitable amount. Preferably, the amount of the second alkaline substance is about 0.01 to about 0.9 (e.g., about 0.02, about 0.05, about 0.07, about 0.1, about 0.2, about 0.3, about 0.4, about 0.5, about 0.6, about 0.7, about 0.8) mole equivalent of ibuprofen, and more preferably about 0.05 to about 0.2 mole equivalent of ibuprofen.

The second alkaline material is used as a solution in water or in a water/alcohol mixture. A water solution is preferred. The hydroxide concentration in solution is about 5% to about 50% (e.g., about 10%, about 15%, about 20%, about 25%, about 30%, about 35%, about 40%, about 45%) by weight, preferably about 20% to about 40% by weight.

The solution of the second alkaline substance is then mixed or kneaded with the mixture of the ibuprofen and the first alkaline substance using high or low shear mixers or granulators known in the art. The use of a planetary-type mixer is preferred. The weight of the second alkaline material solution is about 5% to about 20% (e.g., about 6%, about 7%, about 8%, about 9%, about 10%, about 11%, about 12%, about 13%, about 14%, about 15%, about 16%, about 17%, about 18%, about 19%, and ranges thereof) of the total weight of ibuprofen-first alkaline substance mixture.

Without being bound by any particular mechanism, the transformation process of ibuprofen powder (low density powder of small particle size) into ibuprofen concentrate (high density solid of larger particle size) involves an initial surface reaction between the second alkaline material solution and the solid ibuprofen. The reaction self-progresses as a result of generating molecular water in which the first alkaline substance is soluble, allowing the first alkaline substance to be in solution and interact with the ibuprofen powder. The reaction further propagates when the reaction of the first alkaline substance releases carbonic acid that dissociates into another molecule of water and carbon dioxide. The internal release of molecular water not only allows the in-situ formation of ibuprofen salt but also acts as a liquid bridge in which saturated solution of ibuprofen salt is formed.

The wet ibuprofen concentrate resulting from the second mixing step can be dried directly or after a sieving step. Preferably, the ibuprofen concentrate is sieved (e.g., through a 10-40 mesh screen) before drying. Drying of the ibuprofen concentrate can be achieved by any suitable manner, such as by forced air ovens, convection ovens, or fluid bed driers. Drying is complete when the ibuprofen concentrate moisture content is about 0.1% to 3% (e.g., about 0.2%, about 0.5%, about 0.7%, about 1%, about 1.2%, about 1.5%, about 1.7%), and preferably about 0.2% to about 2%.

The dried ibuprofen concentrates have improved physical properties compared to the ibuprofen known in the art. For example, the ibuprofen concentrates of the invention have a higher bulk density, larger particle size, and lesser amount of fines than ibuprofen powder. These advantages make the ibuprofen concentrates of the invention an exceptional material for making solid dosage forms, such as tablets and capsules, where easier processing and better quality finished products can be achieved.

The solid ibuprofen concentrate can have any suitable bulk density. Preferably, the bulk density of the solid ibuprofen concentrate is at least about 0.3 g/mL (e.g., at least about 0.4 g/mL, at least about 0.5 g/mL, at least about 0.6 g/mL, at least about 0.7 g/mL, at least about 0.9 g/mL, at least about 1 g/mL, at least about 1.5 g/mL, or at least about 2 g/mL).

The solid ibuprofen concentrate of the invention can have any suitable dissolution profile. Preferably, at least about 85% (e.g., about 87%, about 90%, about 92%, about 95%, about 97%, about 98%, about 99%, or ranges thereof) of the ibuprofen solid concentrate dissolves after about 30 minutes in any suitable dissolution medium. The ibuprofen solid concentrate may optionally be formulated in any suitable dosage form to achieve this dissolution rate, for example, in a soft gelatin capsule. The dissolution rate of the solid ibuprofen concentrate may be measured by any suitable method in any suitable medium. For example, a USP dissolution apparatus type II may be used. The dissolution medium may be, for example, purified water, gastric fluid or a potassium phosphate buffer having a pH of 7.2 containing 1% pancreatin (supplied by Sigma-Aldrich). Preferably, at least about 85% of the solid ibuprofen concentrate dissolves in about 20 minutes. More preferably, at least about 90% of the solid ibuprofen concentrate dissolves in about 15 minutes.

Typically, the solid ibuprofen concentrate is more soluble than ibuprofen powder (i.e., ibuprofen free acid) in any suitable dissolution medium, for example, purified water. Preferably, the solid ibuprofen concentrate is about 2 to about 10 (e.g., about 3, about 4, about 5, about 6, about 7, about 8, about 9, or ranges thereof) times more soluble than ibuprofen powder. More preferably, the solid ibuprofen concentrate is 3 to 5 times more soluble than ibuprofen powder.

The solid ibuprofen concentrate of the invention has suitable flowability of powder, which is typically measured by the angle of repose, to permit the filling of the concentrate into a finished dosage form, such as tablets or capsules (e.g., hard gelatin capsules). Generally, the solid ibuprofen concentrate has a lower angle of repose and, thus, improved flowability as compared to ibuprofen powder. Preferably, the solid ibuprofen concentrate has an angle of repose of less than about 30° (e.g., less than about 28°, less than about 26°, less than about 25°, less than about 22°, or less than about 20°).

The ibuprofen concentrates of the invention can be formulated into soft gelatin capsules (softgel capsules). Although classified as a solid dosage form, soft gelatin capsules offer a unit-dose liquid dosage encapsulated in an edible shell.

To formulate the softgel capsules, the ibuprofen concentrate is dissolved in a soft capsule vehicle. Any suitable soft capsule vehicle can be used, such as polyethylene glycol or a mixture of polyethylene glycol and water. Preferably, the vehicle is a mixture of polyethylene glycol and water. Polyethylene glycol having any suitable molecular weight can be used. Typically, the polyethylene glycol has a molecular weight of 300 to 1500, and preferably a molecular weight of 400 to 600. Typically, the water is purified when used in the soft capsule vehicle.

The ibuprofen concentrates are soluble in polyethylene glycol without the need of adding surfactants, hydrophilic polymers, or hydroxides, the addition of which decreases the ibuprofen concentration. Additionally, unlike some existing techniques, the dissolution of the ibuprofen concentrates in polyethylene glycol does not require excessive heating for a long time, which can cause drug degradation and/or interaction with the vehicle, forming polyethylene glycol-ibuprofen esters.

Total ibuprofen esters formed when preparing softgel fills from the ibuprofen concentrates is less than about 0.2% (e.g., less than about 0.18%, less than about 0.16%, less than about 0.15%, less than about 0.14%, less than about 0.12%, less than about 0.1%, less than about 0.8%, less than about 0.6%, less than about 0.5%, less than about 0.4%, less than about 0.2%, or ranges thereof) and preferably less than about 0.1%.

The softgel fills can be encapsulated into soft gelatin capsules using any suitable mechanism known in the art, such as rotary die technology (see J. P. Stanley, in The Theory and Practice of industrial Pharmacy; Lachman et al., Ed., Philadelphia, 1976).

The gelatin shell can be from any suitable source, such as bovine, porcine, fish, or poultry origin.

The gelatin shell can be of any suitable bloom strength, such as about 100 to about 250 bloom (e.g., about 125 bloom, about 150 bloom, about 175 bloom, about 200 bloom, about 225 bloom) and preferably about 150 bloom.

The gelatin shell can be plasticized with tri- or poly-alcoholic plasticizers such as glycerin, sorbitol, xylitol, or mixtures thereof. A mixture of glycerol and sorbitol is preferred.

The softgel capsules can have any suitable moisture content, such as a total moisture content of less than 10% (e.g., less than about 9%, less than about 8%, less than about 7%, less than about 6%, less than about 5%, or ranges thereof) and preferably less than about 7%.

The invention includes other oral pharmaceuticals manufactured from the ibuprofen concentrate, such as hard shell capsules. Hard shell capsules can be produced by filling the ibuprofen concentrate of the invention into two piece capsules. The two piece capsules also can include lubricants and disintegrating agents as known in the art.

The invention also provides liquid oral pharmaceuticals manufactured from the ibuprofen concentrate, such as liquid suspensions and solutions, drops, and syrups. Liquid oral pharmaceuticals can be prepared by directly dissolving ibuprofen concentrates into a hydrophilic vehicle or a mixture of hydrophilic vehicles, such as water, propylene glycol, and glycerol.

Other adjuvants, such as sweeteners, flavor-enhancing agents, taste masking agents, anti-microbial preservatives, or viscosity imparting agents, can also be used in the pharmaceuticals as known in the art.

Suitable sweeteners include, for example, saccharin sodium, sucrose, sorbitol, aspartame, and mannitol, or mixtures thereof.

Suitable flavoring agents include grape flavor, cherry flavor, cotton candy flavor, or other suitable flavor to make the liquid pharmaceutical easier for a patient to ingest. The flavoring agent or mixtures thereof are typically present in an amount of from about 0.0001 wt % to about 5 wt %.

Suitable anti-microbial preservatives include, for example, methylparaben, propylparaben, sodium benzoate, benzalkonium chloride, or mixtures thereof. The preservative or mixtures thereof are typically present in an amount of from about 0.0001 wt % to about 2 wt %.

Alternatively, ibuprofen concentrates can be used as powder for re-constitution with one or more adjuvants. Solutions made from ibuprofen concentrates have the advantage of tolerating the addition of water at 10-100% of its weight without precipitation.

The ibuprofen concentrates of the invention can be formulated into oral pharmaceuticals at any suitable dose. For example, the ibuprofen concentrates can be formulated into solid dosage forms with ibuprofen dosages of 50 mg, 100 mg, 200 mg, 300 mg, 400 mg, 500 mg, 600 mg, 800 mg, and ranges thereof. For example, the ibuprofen concentrates can be formulated into a tablet containing the equivalent of about 200 mg to about 800 mg ibuprofen per tablet (based on the free acid). The ibuprofen concentrates also can be formulated into a hard shell or soft shell capsule containing the equivalent of about 200 mg to about 400 mg per capsule (based on the free acid).

The ibuprofen concentrates also can be formulated into liquid suspensions or solutions at any suitable ibuprofen dose. Generally, the liquid concentrates can be formulated with ibuprofen concentrations of 1 mg/mL to 1000 mg/mL (e.g., 10 mg/mL, 20 mg/mL, 30 mg/mL, 40 mg/mL, 50 mg/mL, 60 mg/mL, 80 mg/mL, 100 mg/mL, 200 mg/mL, 300 mg/mL, 500 mg/mL, 550 mg/mL, 700 mg/mL, 800 mg/mL, and ranges thereof). Preferably, the liquid concentrates have ibuprofen concentrates of 10 mg/mL to about 500 mg/mL, and more preferably 20 mg/mL to 40 mg/mL.

The following examples further illustrate the invention but, of course, should not be construed as in any way limiting its scope.

EXAMPLE 1

This example demonstrates the preparation of a solid ibuprofen concentrate of the invention.

A 2590 g batch of ibuprofen concentrate was prepared using the following ingredients.

| Ingredient | Amount (g) |
|---|---|
| Ibuprofen USP | 2000 |
| Potassium bicarbonate | 120 |
| Potassium carbonate anhydrous, NF | 270 |
| Potassium hydroxide aqueous solution 33% (w/w) | 200 |

In this example, ibuprofen was dry-mixed with potassium bicarbonate and potassium carbonate anhydrous in planetary (Hobart) mixer for 5 min. The blended composition was mixed with potassium hydroxide aqueous solution 33% (w/w) for 5 minutes and the wet concentrate was dried at 45° C.±5° C. in a drying oven. Dried ibuprofen concentrate was then passed through #40 mesh screen.

The resultant ibuprofen concentrate had a final moisture content of 2% and a bulk density of 0.4 g/mL.

EXAMPLE 2

This example demonstrates the preparation of a solid ibuprofen concentrate of the invention.

A 2470 g batch of ibuprofen concentrate was prepared using the following ingredients:

| Ingredient | Amount (g) |
|---|---|
| Ibuprofen USP | 2000 |
| Potassium carbonate anhydrous, NF | 270 |
| Potassium hydroxide aqueous solution 33% (w/w) | 200 |

Ibuprofen concentrate was prepared as set forth in Example 1.

The resultant ibuprofen concentrate had a final moisture content of about 2% and a bulk density of about 0.4 g/mL.

EXAMPLE 3

This example demonstrates the preparation of a solid ibuprofen concentrate of the invention.

A 30 kg batch of ibuprofen concentrate was prepared using the following ingredients.

| Ingredient | Amount (kg) |
|---|---|
| Ibuprofen USP | 24.292 |
| Potassium carbonate anhydrous, NF | 3.279 |
| Potassium hydroxide aqueous solution 33% (w/w) | 2.429 |

Ibuprofen concentrate was prepared as set forth in Example 1.

The resultant ibuprofen concentrate had a final moisture content of about 1.8% and a bulk density of about 0.41 g/mL.

EXAMPLE 4

This example demonstrates the preparation of a solid ibuprofen concentrate of the invention.

A 3000 g batch of ibuprofen concentrate was prepared using the following ingredients.

| Ingredient | Amount (g) |
|---|---|
| Ibuprofen USP | 2222 |
| Potassium bicarbonate | 667 |
| Purified water | 111 |

Ibuprofen concentrate was prepared as set forth in Example 1.

The resultant ibuprofen concentrate had a final moisture content of about 1.8% and a bulk density of about 0.41 g/mL.

EXAMPLE 5

This example demonstrates the preparation of an oral 40 mg/mL solution of the solid ibuprofen concentrate.

A 25 g batch of ibuprofen oral solution was prepared with the following ingredients.

| Ingredient | Amount (g) |
|---|---|
| Ibuprofen concentrate from Example 3 | 1.0 |
| Polyethylene glycol 600 (PEG 600) | 10.0 |
| Purified water, USP | 14.0 |

The ibuprofen concentrate from Example 3 was dissolved in polyethylene glycol 600 and purified water at 40° C.±5° C.

The resultant clear solution was cooled to room temperature and had a pH 8.0.

EXAMPLE 6

This example demonstrates the preparation of a solution of the solid ibuprofen concentrate.

A 3000 g batch of ibuprofen softgel capsules fill material was prepared from ibuprofen concentrate using the following ingredients.

| Ingredient | Amount (g) |
|---|---|
| Ibuprofen concentrate from Example 1 | 1131.10 |
| Polyethylene glycol 600, NF (PEG 600) | 1838.35 |

The ibuprofen concentrate from Example 1 was dissolved in polyethylene glycol 600 at 35° C.±5° C. The solution was cooled to room temperature and de-aerated under vacuum.

The resultant fill material was clear and had an ibuprofen concentrate equivalent to 200 mg of ibuprofen free acid per 600 mg solution and an ester content of less than 0.02%.

EXAMPLE 7

This example demonstrates the preparation of a solution of the solid ibuprofen concentrate.

A 1800 g batch of ibuprofen softgel capsules fill material was prepared from ibuprofen concentrate using the following ingredients.

| Ingredient | Amount (g) |
| --- | --- |
| Ibuprofen concentrate from Example 1 | 678.66 |
| Polyethylene glycol 600, NF (PEG 600) | 1121.34 |
| Purified water, USP | 195.0 |

The ibuprofen concentrate from Example 1 was dissolved in polyethylene glycol 600 and purified water at 35° C.±5° C. The solution was cooled to room temperature and de-aerated under vacuum.

The resultant fill material was clear and had an ibuprofen concentrate equivalent to 200 mg of ibuprofen free acid per 600 mg solution and an ester content less than 0.02%.

EXAMPLE 8

This example demonstrates the preparation of a solution of the solid ibuprofen concentrate.

A 3000 g batch of ibuprofen softgel capsules fill material was prepared from ibuprofen concentrate using the following ingredients.

| Ingredient | Amount (g) |
| --- | --- |
| Ibuprofen concentrate from Example 1 | 1131.10 |
| Polyethylene glycol 600, NF (PEG 600) | 1838.50 |
| Purified water, USP | 117.0 |

The ibuprofen concentrate from Example 1 was dissolved in polyethylene glycol 600 and purified water at 35° C.±5° C. The solution was cooled to room temperature and de-aerated under vacuum.

The resultant fill material was clear and had an ibuprofen concentrate equivalent to 200 mg of ibuprofen free acid per 600 mg solution and an ester content of less than 0.02%.

EXAMPLE 9

This example demonstrates the preparation of a solution of the solid ibuprofen concentrate.

A 3000 gram batch of ibuprofen softgel capsules fill material was prepared from ibuprofen concentrate using the following ingredients.

| Ingredient | Amount (g) |
| --- | --- |
| Ibuprofen concentrate from Example 2 | 1174.40 |
| Polyethylene glycol 600, NF (PEG 600) | 1825.60 |
| Purified water, USP | 117.0 |

The ibuprofen concentrate from Example 2 was dissolved in polyethylene glycol 600 and purified water at 35° C.±5° C. The solution was cooled to room temperature and de-aerated under vacuum.

The resultant fill material was clear and had an ibuprofen concentrate equivalent to 200 mg of ibuprofen free acid per 600 mg solution and an ester content of less than 0.02%.

EXAMPLE 10

This example demonstrates the formulation of the ibuprofen concentrate in soft gelatin capsules.

A 1800 g batch of ibuprofen softgel capsules fill material was prepared from ibuprofen concentrate using the following ingredients.

| Ingredient | Amount (g) |
| --- | --- |
| Ibuprofen concentrate from Example 2 | 683.37 |
| Polyethylene glycol 600, NF (PEG 600) | 999.63 |
| Purified water, USP | 117.0 |

The ibuprofen concentrate from Example 2 was dissolved in polyethylene glycol 600 and purified water at 35° C.±5° C. The solution was cooled to room temperature and de-aerated under vacuum.

The resultant fill material was clear and had an ibuprofen concentrate equivalent to 200 mg of ibuprofen free acid per 600 mg solution and an ester content of less than 0.02%.

The resultant fill material was encapsulated into 11 oblong soft gelatin capsules using a Bochang rotary die encapsulator and 150 bloom, limed bone, plasticized gelatin.

EXAMPLE 11

This example demonstrates the formulation of the ibuprofen concentrate in soft gelatin capsules.

A 3000 g batch of ibuprofen softgel capsules fill material was prepared from ibuprofen concentrate using the following ingredients.

| Ingredient | Amount (g) |
| --- | --- |
| Ibuprofen concentrate from Example 2 | 1138.95 |
| Polyethylene glycol 600, NF (PEG 600) | 1666.05 |
| Purified water, USP | 195.0 |

The ibuprofen concentrate from Example 2 was dissolved in polyethylene glycol 600 and purified water at 35° C.±5° C. The solution was cooled to room temperature and de-aerated.

The resultant fill material was clear and had an ibuprofen concentrate equivalent to 200 mg of ibuprofen free acid per 600 mg solution and an ester content of less than 0.02%.

The fill material was encapsulated into 11 oblong soft gelatin capsules using a Bochang rotary die encapsulator and 150 bloom Plasticized Type B bovine gelatin as in Example 10.

EXAMPLE 12

This example demonstrates the formulation of the ibuprofen concentrate in soft gelatin capsules.

A 54000 g batch of ibuprofen softgel capsules fill material was prepared from ibuprofen concentrate using the following materials.

| Ingredient | Amount (g) |
|---|---|
| Ibuprofen concentrate from Example 3 | 20250 |
| Polyethylene glycol 600, NF (PEG 600) | 30240 |
| Purified water, USP | 3510 |

The ibuprofen concentrate from Example 3 was dissolved in polyethylene glycol 600 and purified water at 45° C.±5° C. The solution was cooled to room temperature and de-aerated.

The resultant fill material was clear and had an ibuprofen concentrate equivalent to 200 mg of ibuprofen free acid per 600 mg solution and an ester content of less than 0.02%.

The fill material was encapsulated into 11 oblong soft gelatin capsules using a Bochang rotary die encapsulator and 150 bloom Plasticized Type B bovine gelatin as in Example 10.

EXAMPLE 13

This example demonstrates the preparation of a solution of the solid ibuprofen concentrate.

2 kg of the fill material of Example 12 was heated to 50° C.±5° C. for 120 minutes. Then the solution was cooled to room temperature and de-aerated under vacuum.

The resultant fill material was clear and had an ibuprofen concentrate equivalent to 200 mg of ibuprofen free acid per 600 mg solution and an ester content of less than 0.02%.

EXAMPLE 14

This example demonstrates the formulation of the ibuprofen concentrate in soft gelatin capsules.

10 kg of the fill material of Example 12 was heated to 60° C.±5° C. for 120 minutes. Then the solution was cooled to room temperature and de-aerated.

The resultant fill material was clear and had an ibuprofen concentrate equivalent to 200 mg of ibuprofen free acid per 600 mg solution and an ester content of less than 0.02%.

The fill material was encapsulated into 11 oblong soft gelatin capsules using Bochang rotary die encapsulator and 150 bloom Plasticized Type B bovine gelatin as in example 10.

EXAMPLE 15

This example demonstrates the preparation of a solution of the solid ibuprofen concentrate.

A 3000 g batch of Ibuprofen softgel capsules fill material was prepared from ibuprofen concentrate using the following ingredients.

| Ingredient | Amount (g) |
|---|---|
| Ibuprofen concentrate from Example 4 | 1204.75 |
| Polyethylene glycol 600, NF (PEG 600) | 1795.25 |

The ibuprofen concentrate from Example 4 was dissolved in polyethylene glycol 600 at 50° C.±5° C. The solution was cooled to room temperature and de-aerated.

The resultant fill material was clear and had an ibuprofen concentrate equivalent to 200 mg of ibuprofen free acid per 600 mg solution and an ester content of less than 0.02%.

EXAMPLE 16

This example demonstrates the preparation of a solution of the solid ibuprofen concentrate.

A 100 g batch of ibuprofen softgel capsules fill material was prepared from ibuprofen concentrate using the following ingredients.

| Ingredient | Amount (g) |
|---|---|
| Ibuprofen concentrate from Example 3 | 51.25 |
| Polyethylene glycol 600, NF (PEG 600) | 41.9 |
| Purified water, USP | 6.6 |

Ibuprofen concentrate from Example 3 was dissolved in polyethylene glycol 600 and purified water at 55° C.±5° C. The solution was cooled to room temperature and de-aerated. The resultant clear solution was diluted with 20% w/w water without precipitation.

Each 0.600 g of fill material contained 400 mg of ibuprofen.

EXAMPLE 17

This example demonstrates the preparation of a solution of the solid ibuprofen concentrate.

A 100 g batch of ibuprofen softgel capsules fill material was prepared from ibuprofen concentrate using the following ingredients.

| Ingredients Name | Amount (g) |
|---|---|
| Ibuprofen concentrate from Example 3 | 57.60 |
| Polyethylene glycol 600, NF (PEG 600) | 35.8 |
| Purified water, USP | 6.6 |

The ibuprofen concentrate from Example 3 was dissolved in polyethylene glycol 600 and purified water at 55° C.±5° C. The solution was cooled to room temperature and de-aerated. The resultant clear solution was diluted with 20% w/w water without precipitation.

Each 0.750 g fill material contained 400.00 mg ibuprofen.

EXAMPLE 18

This example demonstrates formulations of the solid ibuprofen concentrate into tablets.

In this example, the ibuprofen concentrate product of Example 3 was further dried at 45° C.±5° C. to a moisture content of 0.8%. The dried granules were lubricated with 0.25% w/w magnesium stearate and compressed using a Piccola 10 station rotary tablet press. The lubricated granules had angle of repose 26.56° compared with ibuprofen powder (supplied by BASF) having an angle of repose 48.01°. The resultant compressed tablets had hardness 6.1 kp and thickness 4.80 mm.

EXAMPLE 19

This example shows the comparative dissolution profile of the solid ibuprofen concentrate as compared to ibuprofen powder.

Ibuprofen concentrate made according to Example 3 or ibuprofen powder (i.e., ibuprofen free acid) was filled manually into size 1 hard gelatin capsules to yield 200 mg ibuprofen per capsule. Ibuprofen powder (supplied by BASF) was similarly filled manually into size 1 hard gelatin capsules to yield 200 mg ibuprofen per capsule.

Capsules were tested using a USP dissolution apparatus type II with a paddle speed of 50 rpm and 900 mL of purified water as a dissolution medium. The solid ibuprofen concentrate of the invention was 3 to 5 times more soluble in water than ibuprofen powder.

| Time (min) | % dissolution of ibuprofen concentrate | % dissolution of ibuprofen powder |
|---|---|---|
| 10 | 12.0 | 2.2 |
| 20 | 23.2 | 5.9 |
| 30 | 28.5 | 9.2 |

EXAMPLE 20

This example demonstrates the fast dissolution rate of soft gelatin capsules containing the solid ibuprofen concentrate of the invention.

Capsules made according to Example 12 and containing ibuprofen concentrate equivalent to 200 mg ibuprofen were tested using a USP dissolution apparatus type II with a paddle speed of 50 rpm and 900 mL of potassium phosphate buffer (at a pH of 7.2) containing 1% pancreatin (supplied by Sigma-Aldrich).

| Time (min) | % w/w ibuprofen dissolved |
|---|---|
| 15 | 92.3 |
| 20 | 95.5 |
| 30 | 97.8 |
| 45 | 98.9 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a solid ibuprofen concentrate, wherein the solid ibuprofen concentrate comprises (a) a solid ibuprofen free acid and (b) a solid ibuprofen alkali salt, and wherein at least 90% of the weight of the solid ibuprofen concentrate is ibuprofen free acid and ibuprofen alkali salt.

2. The composition of claim 1, wherein at least 92% of the weight of the solid ibuprofen concentrate is ibuprofen free acid and ibuprofen alkali salt.

3. The composition of claim 1, wherein at least 95% of the weight of the solid ibuprofen concentrate is ibuprofen free acid and ibuprofen alkali salt.

4. The composition of claim 1, wherein at least 97% of the weight of the solid ibuprofen concentrate is ibuprofen free acid and ibuprofen alkali salt.

5. The composition of claim 1, wherein the solid ibuprofen concentrate has a bulk density of at least 0.3 g/mL.

6. The composition of claim 1, wherein the solid ibuprofen concentrate is soluble in polyethylene glycol.

7. The composition of claim 1, wherein the composition is a hard shell capsule, soft gelatin capsule, liquid suspension, liquid solution, or tablet.

8. The composition of claim 7, wherein the composition is a tablet.

9. The composition of claim 8, equivalent to about 200 to about 800 mg ibuprofen per tablet.

10. The composition of claim 7, wherein the composition is a solution.

11. The composition of claim 10, equivalent to about 10 mg to about 50 mg ibuprofen per mL.

12. The composition of claim 7, wherein the composition is a soft gelatin capsule.

13. The composition of claim 12, equivalent to about 200 mg to about 400 mg ibuprofen per capsule.

14. The composition of claim 7, wherein the composition is a hard shell capsule.

15. The composition of claim 14, equivalent to about 200 mg to about 400 mg ibuprofen per capsule.

16. The composition of claim 1, wherein at least 85% of the solid ibuprofen concentrate dissolves within in 30 minutes.

17. The composition of claim 16, wherein at least 85% of the solid ibuprofen concentrate dissolves within in 20 minutes.

18. The composition of claim 1, wherein the solid ibuprofen alkali salt is an ibuprofen potassium salt, ibuprofen sodium salt, or ibuprofen ammonium salt or a mixture thereof.

19. The composition of claim 18, wherein the solid ibuprofen alkali salt is an ibuprofen potassium salt.

20. A method of manufacturing a solid ibuprofen concentrate, wherein at least 90% of the weight of the ibuprofen concentrate is ibuprofen free acid and ibuprofen alkali salt, comprising:
   (a) mixing an ibuprofen free acid with a first alkaline substance to form a first composition,
   (b) mixing the first composition with a second alkaline substance to form a second composition, and
   (c) drying the second composition to produce a solid ibuprofen concentrate.

21. The method of claim 20, further comprising sieving the second composition prior to drying.

22. The method of claim 20, wherein the first alkaline substance is selected from the group consisting of a carbonate species, a bicarbonate species, and mixtures thereof.

23. The method of claim 22, wherein the first alkaline substance is a carbonate species selected from the group consisting of ammonium carbonate, ammonium bicarbonate, potassium carbonate, potassium bicarbonate, sodium carbonate, and sodium bicarbonate.

24. The method of claim 23, wherein the first alkaline substance is potassium carbonate.

25. The method of claim 20, wherein the second alkaline substance comprises a hydroxide species.

26. The method of claim 25, wherein the hydroxide species is selected from the group consisting of ammonium hydroxide, potassium hydroxide, and sodium hydroxide.

27. The method of claim 26, wherein the hydroxide species is potassium hydroxide.

28. The method of claim 22, wherein the ibuprofen alkali salt is ibuprofen potassium salt.

29. The method of claim 20, further comprising filling the solid ibuprofen concentrate in hard shell capsules.

30. A solid ibuprofen concentrate obtained by the method of claim 20.

31. A method of formulating the composition of claim 1 into a soft gelatin capsule comprising:
   (a) dissolving the ibuprofen concentrate in a soft capsule vehicle to form a soft gelatin fill, and
   (b) encapsulating the soft gelatin fill in a soft gelatin capsule.

32. The method of claim 31, wherein the soft capsule vehicle is polyethylene glycol.

33. The method of claim 31, wherein the soft capsule vehicle is selected from the group consisting of polyethylene glycol or a polyethylene glycol-water mixture.

34. The method of claim 31, wherein the amount of ibuprofen-esters formed is less than about 0.2%.

35. A composition comprising a solid ibuprofen concentrate, wherein the solid ibuprofen concentrate comprises (a) a solid ibuprofen free acid and (b) a solid ibuprofen alkali salt, and wherein at least 90% of the weight of the solid ibuprofen concentrate is ibuprofen free acid and ibuprofen alkali salt, wherein the ibuprofen alkali salt is produced from a solid ibuprofen free acid using at least two alkaline substances.

36. The composition of claim 35, wherein at least 95% of the weight of the solid ibuprofen concentrate is ibuprofen free acid and ibuprofen alkali salt.

37. The composition of claim 35, wherein the composition is a hard shell capsule, soft gelatin capsule, liquid suspension, liquid solution, or tablet.

38. The composition of claim 37, wherein the solid ibuprofen alkali salt is an ibuprofen potassium salt.

* * * * *

UNITED STATES PATENT AND TRADEMARK OFFICE
CERTIFICATE OF CORRECTION

PATENT NO. : 7,582,679 B2  
APPLICATION NO. : 11/346975  
DATED : September 1, 2009  
INVENTOR(S) : Hassan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

Fourteenth Day of December, 2010

David J. Kappos  
*Director of the United States Patent and Trademark Office*